United States Patent
Matozaki et al.

(10) Patent No.: US 7,449,301 B2
(45) Date of Patent: Nov. 11, 2008

(54) PHARMACEUTICAL COMPOSITION AND METHOD FOR ACTIVATING MACROPHAGE USING THE SAME

(75) Inventors: Takashi Matozaki, Maebashi (JP); Hiroshi Ohnishi, Maebashi (JP)

(73) Assignee: National University Corporation Gunma University, Gunma (JP)

( * ) Notice: Subject to any disclaimer, the term of this patent is extended or adjusted under 35 U.S.C. 154(b) by 0 days.

(21) Appl. No.: 10/996,628

(22) Filed: Nov. 23, 2004

(65) Prior Publication Data

US 2005/0244415 A1    Nov. 3, 2005

(30) Foreign Application Priority Data

Apr. 28, 2004    (JP)    ............... 2004-133599

(51) Int. Cl.
*G01N 33/53*    (2006.01)
(52) U.S. Cl. ....................................... 435/7.1
(58) Field of Classification Search .............. 424/9.1, 424/130.1; 435/4, 7.23
See application file for complete search history.

(56) References Cited

FOREIGN PATENT DOCUMENTS

| | | |
|---|---|---|
| JP | 63-126827 | 5/1988 |
| JP | 05-097695 | 4/1993 |
| WO | 00/66159 | 11/2000 |

OTHER PUBLICATIONS

Freshney, Culture of animal cells, a manual of basic technique, Alan R. Liss, Inc., New York 1983, pp. 3-4.*
Dermer, Another anniversary for the war on cancer, Bio/Technology, Mar. 1994 vol. 12, p. 320.*
Jain, Barrier to drug delivery in solid tumors, Scientific American, Jul. 1994, pp. 58-65.*
Dillman, MOnoclonal antibodies for treating cancer, Annals of Internal Medicine, 1989, vol. 111, pp. 592-603.*
Weiner, A overview of monoclonal antibody therapy of cancer, Seminars in Oncology, Aug. 1999, vol. 26, No. 4, Suppl 12, pp. 41-50.*
Gura, Systems for indetifying new drugs are often faulty, Science, Nov. 1997, vol. 278, pp. 1041-1042.*
White et al, Annu Rev Med 52:125-145, 2001.*
Unkeless et al., JEM, 1974, 139:834-850).*
Barclay et al., Nature Reviews, Immunology, 2006, 6:457-464.*
Hayashi et al JBC, Jul. 9, 2004, 279:29450-29460.*
Nature, vol. 386, Mar. 13, 1997, p. 181-186.
Blood, vol. 97, May 1, 2001, No. 9, p. 2741-2749.

\* cited by examiner

*Primary Examiner*—Misook Yu
*Assistant Examiner*—Mark Halvorson
(74) *Attorney, Agent, or Firm*—Hogan & Hartson LLP (57) ABSTRACT

A pharmaceutical composition is produced by obtaining an antibody which specifically recognizes an extracellular domain of SIRPβ and formulating the antibody with a pharmaceutical acceptable carrier. The patient suffering from infectious disease or cancer is treated by administering the pharmaceutical composition to activate macrophages.

1 Claim, 7 Drawing Sheets

SEQUENCE LISTING

```
<160> NUMBER OF SEQ ID NOS: 8

<210> SEQ ID NO 1
<211> LENGTH: 1232
<212> TYPE: DNA
<213> ORGANISM: Mus musculus
<220> FEATURE:
<221> NAME/KEY: CDS
<222> LOCATION: (23)..(1198)
<223> OTHER INFORMATION:

<400> SEQUENCE: 1
aacagggttc ttaacaccaa cc atg ctt ctc cta gat gcc tgg acc cac att    52
                         Met Leu Leu Leu Asp Ala Trp Thr His Ile
                          1               5                  10
```

-continued

| | |
|---|---:|
| cct cac agt gtc ctg ctg ttg atc ctg ctt ctg gga ttt aaa gga gca<br>Pro His Ser Val Leu Leu Leu Ile Leu Leu Leu Gly Phe Lys Gly Ala<br>                15                     20              25 | 100 |
| gct gtg aga gag ctg aaa gtg atc caa cct gtt aaa tca ttt ttt gtt<br>Ala Val Arg Glu Leu Lys Val Ile Gln Pro Val Lys Ser Phe Phe Val<br>        30                   35                  40 | 148 |
| ggt gct gga ggg tca gcc act cta aac tgc aca gtg aca tcc ctc ctc<br>Gly Ala Gly Gly Ser Ala Thr Leu Asn Cys Thr Val Thr Ser Leu Leu<br>          45                   50                55 | 196 |
| cct gtg ggg ccc ata agg tgg tat agg ggt gta gga caa agt cga ctc<br>Pro Val Gly Pro Ile Arg Trp Tyr Arg Gly Val Gly Gln Ser Arg Leu<br>       60                65                70 | 244 |
| ttg ata tac ccg ttc aca gga gaa cat tcc ccc cga ata aca aat gtt<br>Leu Ile Tyr Pro Phe Thr Gly Glu His Ser Pro Arg Ile Thr Asn Val<br>75                80                85                90 | 292 |
| tca gat gtt aca aag aga aac aac atg gac ttt tcc atc cgt atc agt<br>Ser Asp Val Thr Lys Arg Asn Asn Met Asp Phe Ser Ile Arg Ile Ser<br>               95                 100            105 | 340 |
| aat gtc act cct gct gat tcg ggt acc tac tac tgt gtg aag ttc cag<br>Asn Val Thr Pro Ala Asp Ser Gly Thr Tyr Tyr Cys Val Lys Phe Gln<br>            110                115            120 | 388 |
| aga gga tca tca gag cct gac att gag att cag tct gga ggt ggc act<br>Arg Gly Ser Ser Glu Pro Asp Ile Glu Ile Gln Ser Gly Gly Gly Thr<br>          125                130               135 | 436 |
| gag ttg tta gtc ctt gct aaa cca tct tca cct atg gtc tcc ggt cct<br>Glu Leu Leu Val Leu Ala Lys Pro Ser Ser Pro Met Val Ser Gly Pro<br>      140                145               150 | 484 |
| gca gcc aga gct gtc cct cag cag aca gtg acc ttt aca tgc aga tcc<br>Ala Ala Arg Ala Val Pro Gln Gln Thr Val Thr Phe Thr Cys Arg Ser<br>155                160                165            170 | 532 |
| cat gga ttc ttt ccg cgg aac ctc acg ctg aag tgg ttc aag aat gga<br>His Gly Phe Phe Pro Arg Asn Leu Thr Leu Lys Trp Phe Lys Asn Gly<br>               175              180              185 | 580 |
| gat gag atc tct cac ttg gaa act tct gtg gaa ccg gaa gaa aca agt<br>Asp Glu Ile Ser His Leu Glu Thr Ser Val Glu Pro Glu Glu Thr Ser<br>              190              195              200 | 628 |
| gtc tcc tat aga gtt tcc agc aca gtc cag gtg gtg ttg gaa cct agg<br>Val Ser Tyr Arg Val Ser Ser Thr Val Gln Val Val Leu Glu Pro Arg<br>          205                210              215 | 676 |
| gat gtc cgc tct cag atc atc tgt gaa gtg gat cat gtc act tta gat<br>Asp Val Arg Ser Gln Ile Ile Cys Glu Val Asp His Val Thr Leu Asp<br>        220               225              230 | 724 |
| cga gcc cct ctc aga ggg att gct cac atc tct gag ttc att caa gtt<br>Arg Ala Pro Leu Arg Gly Ile Ala His Ile Ser Glu Phe Ile Gln Val<br>235                240                245            250 | 772 |
| cca ccc acc ctg gag atc cgc cag cag cca aca atg gtt tgg aat gtg<br>Pro Pro Thr Leu Glu Ile Arg Gln Gln Pro Thr Met Val Trp Asn Val<br>              255              260              265 | 820 |
| ata aat gtc acc tgc caa ata cag aag ttc tat cct cca agt ttt cag<br>Ile Asn Val Thr Cys Gln Ile Gln Lys Phe Tyr Pro Pro Ser Phe Gln<br>          270                275            280 | 868 |
| ttg acc tgg tta gag aat gga aat ata tcc cgg aga gaa gta cct ttt<br>Leu Thr Trp Leu Glu Asn Gly Asn Ile Ser Arg Arg Glu Val Pro Phe<br>             285              290              295 | 916 |
| aca ctt ata gta aac aag gat gga act tac aac tgg atc agc tgt ctc<br>Thr Leu Ile Val Asn Lys Asp Gly Thr Tyr Asn Trp Ile Ser Cys Leu<br>        300               305              310 | 964 |
| ttg gtg aac ata tct gcc ctt gag gag aac atg gta gtg aca tgc aag<br>Leu Val Asn Ile Ser Ala Leu Glu Glu Asn Met Val Val Thr Cys Lys<br>315                320                325            330 | 1012 |

```
gtt gag cat gat gaa caa gca gaa gtc att gaa acc cat act gtg ctg      1060
Val Glu His Asp Glu Gln Ala Glu Val Ile Glu Thr His Thr Val Leu
                335                 340                 345 gtc act gaa cat cag aga gtg aaa gaa ctg aag acg gca ggt att gct      1108
Val Thr Glu His Gln Arg Val Lys Glu Leu Lys Thr Ala Gly Ile Ala
            350                 355                 360 aaa ata cct gta gct gtg ctc ctt gga tcc aaa ata ctg ctg tta att      1156
Lys Ile Pro Val Ala Val Leu Leu Gly Ser Lys Ile Leu Leu Leu Ile
        365                 370                 375 gct gcc act gtc att tac atg cat aag aag caa aat gcc tga              1198
Ala Ala Thr Val Ile Tyr Met His Lys Lys Gln Asn Ala
    380                 385                 390 ataggctccg aatggaaata agtgctaatg agca                                1232
```

<210> SEQ ID NO 2
<211> LENGTH: 391
<212> TYPE: PRT
<213> ORGANISM: Mus musculus

<400> SEQUENCE: 2

```
Met Leu Leu Leu Asp Ala Trp Thr His Ile Pro His Ser Val Leu Leu
1               5                   10                  15

Leu Ile Leu Leu Leu Gly Phe Lys Gly Ala Ala Val Arg Glu Leu Lys
            20                  25                  30

Val Ile Gln Pro Val Lys Ser Phe Val Gly Ala Gly Gly Ser Ala
        35                  40                  45

Thr Leu Asn Cys Thr Val Thr Ser Leu Leu Pro Val Gly Pro Ile Arg
    50                  55                  60

Trp Tyr Arg Gly Val Gly Gln Ser Arg Leu Leu Ile Tyr Pro Phe Thr
65                  70                  75                  80

Gly Glu His Ser Pro Arg Ile Thr Asn Val Ser Asp Val Thr Lys Arg
                85                  90                  95

Asn Asn Met Asp Phe Ser Ile Arg Ile Ser Asn Val Thr Pro Ala Asp
            100                 105                 110

Ser Gly Thr Tyr Tyr Cys Val Lys Phe Gln Arg Gly Ser Ser Glu Pro
        115                 120                 125

Asp Ile Glu Ile Gln Ser Gly Gly Gly Thr Glu Leu Leu Val Leu Ala
    130                 135                 140

Lys Pro Ser Ser Pro Met Val Ser Gly Pro Ala Ala Arg Ala Val Pro
145                 150                 155                 160

Gln Gln Thr Val Thr Phe Thr Cys Arg Ser His Gly Phe Phe Pro Arg
                165                 170                 175

Asn Leu Thr Leu Lys Trp Phe Lys Asn Gly Asp Glu Ile Ser His Leu
            180                 185                 190

Glu Thr Ser Val Glu Pro Glu Thr Ser Val Ser Tyr Arg Val Ser
        195                 200                 205

Ser Thr Val Gln Val Val Leu Glu Pro Arg Asp Val Arg Ser Gln Ile
    210                 215                 220

Ile Cys Glu Val Asp His Val Thr Leu Asp Arg Ala Pro Leu Arg Gly
225                 230                 235                 240

Ile Ala His Ile Ser Glu Phe Ile Gln Val Pro Pro Thr Leu Glu Ile
                245                 250                 255

Arg Gln Gln Pro Thr Met Val Trp Asn Val Ile Asn Val Thr Cys Gln
            260                 265                 270

Ile Gln Lys Phe Tyr Pro Pro Ser Phe Gln Leu Thr Trp Leu Glu Asn
        275                 280                 285
```

-continued

```
Gly Asn Ile Ser Arg Arg Glu Val Pro Phe Thr Leu Ile Val Asn Lys
        290                 295                 300

Asp Gly Thr Tyr Asn Trp Ile Ser Cys Leu Leu Val Asn Ile Ser Ala
305                 310                 315                 320

Leu Glu Glu Asn Met Val Val Thr Cys Lys Val Glu His Asp Glu Gln
                325                 330                 335

Ala Glu Val Ile Glu Thr His Thr Val Leu Val Thr Glu His Gln Arg
                340                 345                 350

Val Lys Glu Leu Lys Thr Ala Gly Ile Ala Lys Ile Pro Val Ala Val
            355                 360                 365

Leu Leu Gly Ser Lys Ile Leu Leu Ile Ala Ala Thr Val Ile Tyr
        370                 375                 380

Met His Lys Lys Gln Asn Ala
385                 390

<210> SEQ ID NO 3
<211> LENGTH: 3804
<212> TYPE: DNA
<213> ORGANISM: Homo sapiens
<220> FEATURE:
<221> NAME/KEY: CDS
<222> LOCATION: (41)..(1237)
<223> OTHER INFORMATION:

<400> SEQUENCE: 3
cacagacgtt tggacagagc aggctcctaa ggtctccaga atg ccc gtg cca gcc        55
                                             Met Pro Val Pro Ala
                                             1               5 tcc tgg ccc cac ctt cct agt cct ttc ctg ctg atg acg cta ctg ctg       103
Ser Trp Pro His Leu Pro Ser Pro Phe Leu Leu Met Thr Leu Leu Leu
                10                  15                  20 ggg aga ctc aca gga gtg gca ggt gag gac gag cta cag gtg att cag       151
Gly Arg Leu Thr Gly Val Ala Gly Glu Asp Glu Leu Gln Val Ile Gln
            25                  30                  35 cct gaa aag tcc gta tca gtt gca gct gga gag tcg gcc act ctg cgc       199
Pro Glu Lys Ser Val Ser Val Ala Ala Gly Glu Ser Ala Thr Leu Arg
        40                  45                  50 tgt gct atg acg tcc ctg atc cct gtg ggg ccc atc atg tgg ttt aga       247
Cys Ala Met Thr Ser Leu Ile Pro Val Gly Pro Ile Met Trp Phe Arg
    55                  60                  65 gga gct gga gca ggc cgg gaa tta atc tac aat cag aaa gaa ggc cac       295
Gly Ala Gly Ala Gly Arg Glu Leu Ile Tyr Asn Gln Lys Glu Gly His
70                  75                  80                  85 ttc cca cgg gta aca act gtt tca gaa ctc aca aag aga aac aac ctg       343
Phe Pro Arg Val Thr Thr Val Ser Glu Leu Thr Lys Arg Asn Asn Leu
                90                  95                  100 aac ttt tcc atc agc atc agt aac atc acc cca gca gac gcc ggc acc       391
Asn Phe Ser Ile Ser Ile Ser Asn Ile Thr Pro Ala Asp Ala Gly Thr
            105                 110                 115 tac tac tgt gtg aag ttc cgg aaa ggg agc cct gac gac gtg gag ttt       439
Tyr Tyr Cys Val Lys Phe Arg Lys Gly Ser Pro Asp Asp Val Glu Phe
        120                 125                 130 aag tct gga gca ggc act gag ctg tct gtg cgc gcc aaa ccc tct gcc       487
Lys Ser Gly Ala Gly Thr Glu Leu Ser Val Arg Ala Lys Pro Ser Ala
    135                 140                 145 ccc gtg gta tcg ggc cct gcg gtg agg gcc aca cct gag cac aca gtg       535
Pro Val Val Ser Gly Pro Ala Val Arg Ala Thr Pro Glu His Thr Val
150                 155                 160                 165
```

-continued

| | | |
|---|---|---|
| agc ttc acc tgc gag tcc cat ggc ttc tct ccc aga gac atc acc ctg<br>Ser Phe Thr Cys Glu Ser His Gly Phe Ser Pro Arg Asp Ile Thr Leu<br>170                          175                    180 | 583 |
| aaa tgg ttc aaa aat ggg aat gag ctc tca gac ttc cag acc aac gtg<br>Lys Trp Phe Lys Asn Gly Asn Glu Leu Ser Asp Phe Gln Thr Asn Val<br>185                        190                    195 | 631 |
| gac ccc gca gga gac agt gtg tcc tac agc atc cac agc aca gcc agg<br>Asp Pro Ala Gly Asp Ser Val Ser Tyr Ser Ile His Ser Thr Ala Arg<br>200                        205                    210 | 679 |
| gtg gtg ctg acc cgt ggg gac gtt cac tct caa gtc atc tgc gag atg<br>Val Val Leu Thr Arg Gly Asp Val His Ser Gln Val Ile Cys Glu Met<br>215                        220                    225 | 727 |
| gcc cac atc acc ttg cag ggg gac cct ctt cgt ggg act gcc aac ttg<br>Ala His Ile Thr Leu Gln Gly Asp Pro Leu Arg Gly Thr Ala Asn Leu<br>230                        235                    240                    245 | 775 |
| tct gag gcc atc cga gtt cca ccc acc ttg gag gtt act caa cag ccc<br>Ser Glu Ala Ile Arg Val Pro Pro Thr Leu Glu Val Thr Gln Gln Pro<br>                  250                    255                    260 | 823 |
| atg agg gca gag aac cag gca aac gtc acc tgc cag gtg agc aat ttc<br>Met Arg Ala Glu Asn Gln Ala Asn Val Thr Cys Gln Val Ser Asn Phe<br>265                        270                    275 | 871 |
| tac ccc cgg gga cta cag ctg acc tgg ttg gag aat gga aat gtg tcc<br>Tyr Pro Arg Gly Leu Gln Leu Thr Trp Leu Glu Asn Gly Asn Val Ser<br>280                        285                    290 | 919 |
| cgg aca gaa aca gct tcg acc ctc ata gag aac aag gat ggc acc tac<br>Arg Thr Glu Thr Ala Ser Thr Leu Ile Glu Asn Lys Asp Gly Thr Tyr<br>295                        300                    305 | 967 |
| aac tgg atg agc tgg ctc ctg gtg aac acc tgt gcc cac agg gac gat<br>Asn Trp Met Ser Trp Leu Leu Val Asn Thr Cys Ala His Arg Asp Asp<br>310                        315                    320                    325 | 1015 |
| gtg gtg ctc acc tgt cag gtg gag cat gat ggg cag caa gca gtc agc<br>Val Val Leu Thr Cys Gln Val Glu His Asp Gly Gln Gln Ala Val Ser<br>                  330                    335                    340 | 1063 |
| aaa agc tat gcc ctg gag atc tca gca cac cag aag gag cac ggc tca<br>Lys Ser Tyr Ala Leu Glu Ile Ser Ala His Gln Lys Glu His Gly Ser<br>345                        350                    355 | 1111 |
| gat atc acc cat gaa cca gcg ctg gct cct act gct cca ctc ctc gta<br>Asp Ile Thr His Glu Pro Ala Leu Ala Pro Thr Ala Pro Leu Leu Val<br>360                        365                    370 | 1159 |
| gct ctc ctc ctg ggc ccc aag ctg cta ctg gtg gtt ggt gtc tct gcc<br>Ala Leu Leu Leu Gly Pro Lys Leu Leu Leu Val Val Gly Val Ser Ala<br>375                        380                    385 | 1207 |
| atc tac atc tgc tgg aaa cag aag gcc tga ctgaccctca gtctctgctg<br>Ile Tyr Ile Cys Trp Lys Gln Lys Ala<br>390                        395 | 1257 |
| cctcctcctt tcttgagaag ctcagcctga gagaaggagc tggcgagaac cttccccaca | 1317 |
| ctcagctcca aacgcctcct ctcccaggtc atctgcctgc ccacacgctc ctgttccacc | 1377 |
| ttcacaagac catgatgccc caaagcagtg tctctattca cggtcctgag caggggccat | 1437 |
| gggattgggc tctgggcact gactcatggc acctccctag aaggtgagaa acactccaaa | 1497 |
| tctaaacaca ccaggacttc tcccatccgt cgccttggga ctggccataa accacagact | 1557 |
| ctctccaggc tctcaagagt tatcctgtct tctggattcc tgcctacccc aactccccca | 1617 |
| gccttgttga ggttctctac tgcctcctga atacacatga accctatac caattttaag | 1677 |
| aaaaaaatga ttctctttcc tctttgtcca agcatcctat ccctcaaacc caaaagaaa | 1737 |
| gaagctctcc cttctctctc tgtgatggag acagtatttc ttctagtatc ctgcagcctt | 1797 |
| cccagtcctg ctgcttgtgg tagaaattgc tgccacagcc caacattgag gagccctcga | 1857 |

```
tgactgccct ttacaactca tattcagttc tgcctccaaa atgcatgtgt ccacttacat    1917
gagatggtaa atgtttaaca atggactttc tgaaagggaa aaaccaaaag ctgttttgca    1977
gtgcttgcca atttctctag tgtaataact cccaacctga ccaatttcag cactgccaac    2037
agttaaacaa ccagattcga agattcctga aatttaacaa ttggttttca gggcccagtc    2097
caagcctgct gctggaaacc tcagagttaa atccctattc tccacacctc tcacctccac    2157 caccccctccc tgtcccagcc agcatcatct ctttggggac cactcctctg gctttcattt    2217
ttcagccaca gtgattcttt ggaaaagtca aatcatatca cttctctgct tcttccccaa    2277
cacagctgca tggtcccgct ctccctcctt caagtctctg ctcaatgtca cttcattaaa    2337
ggcggccttc tataaactac cttgtataaa atattattta ttttctctat cccggcattc    2397
taatttctct tatcctaatt aattttttctt tagcccttat tttgatgagt attatgccga    2457
atacaggcag ccctcacttt tcatggccag tgcaagattg caaaaagact gtgcaacctg    2517
aaacccagga aagcagtctc catagtcaat cagaaaaaca atgatcattc tgtgaccttt    2577 accattttt gtcaaaatat tagaaactct cacactctca gttacaaatg tagaggacaa    2637
tgaaaatata atgaaataaa tatttatttg tgcactacaa ttcaaagcat tagaaacatt    2697
gaagtcaatg gcgtttcttg taaatgtatc cagatgaggt tggaagagtg cttgacccttt    2757 ttgtatattt ctaatatgga gtgatatagt ttggctctgt gtctccatcc aaatctcatc    2817
ttaaattgta atctgcatgt gttgtgggaa tgggacctag gtaggaggtg actgaataca    2877
tgggggcgga cttccccctt gctgttcttg tgatagtgag ttctcataag atctcagtga    2937
gttctcatga gatctggttt tttgaaagtg tgtggcaagt ccccccttcgc tctctctctc    2997 tctctccctc ctgccaccat gtgaagaagg tgcctgcttc cttttctcct tccaccatgg    3057
ttgtaagttt cctgaggcct cccagtcatg cttcctgtta agcctgtgga actgtgagtc    3117
caattaaacc tcttttattc ataaaatatc cagtttctgg tagttcttta tagcagtgtg    3177
agaatgggct aatacacgga gcaagcatcg ttctttcatt tttatttatt ttattttttg    3237
agatggagtt tcaccttatt cccaggctgg agtgcaatgt cgtgatcttg gctcactgca    3297
acccccgcct ccagggttca agtgattctc ctgcctcagc ctcctgagta gctgggatta    3357
caggcatgta ccaccacacc cagctaattt tgtatttta gtagagatgg ggtttctcca    3417
tgttgatcag actagtcttg aactcccgac ctcaggtgat ccacctgtct tggcctccca    3477
aagtgctggg attacaggca tgagccacca tgcctagcca gcaagcatca tttctattat    3537
accttggtgt ttgcctcttt ctaagtttgg actagcttcc aacatcttat cccttgaatt    3597
ttcaatattg tggaatcact ccagaagatc ctttcatgtg aagttttttg ctggcatttc    3657
aacctttggg acatcttcag ccctttatt accactcctc tcccatttgt ggcagtttgc    3717
gtttactacc tccctctggc tgcctatctg aagttcctgc atcagggtct acattgccac    3777
agtcaactat ttgtacttct agaattc                                       3804
```

<210> SEQ ID NO 4
<211> LENGTH: 398
<212> TYPE: PRT
<213> ORGANISM: Homo sapiens

<400> SEQUENCE: 4

Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Asp Glu
            20                  25                  30

-continued

```
Leu Gln Val Ile Gln Pro Glu Lys Ser Val Ser Val Ala Ala Gly Glu
         35                  40                  45

Ser Ala Thr Leu Arg Cys Ala Met Thr Ser Leu Ile Pro Val Gly Pro
 50                  55                  60

Ile Met Trp Phe Arg Gly Ala Gly Ala Arg Glu Leu Ile Tyr Asn
 65                  70                  75                  80

Gln Lys Glu Gly His Phe Pro Arg Val Thr Thr Val Ser Glu Leu Thr
                     85                  90                  95

Lys Arg Asn Asn Leu Asn Phe Ser Ile Ser Ile Ser Asn Ile Thr Pro
                100                 105                 110

Ala Asp Ala Gly Thr Tyr Tyr Cys Val Lys Phe Arg Lys Gly Ser Pro
            115                 120                 125

Asp Asp Val Glu Phe Lys Ser Gly Ala Gly Thr Glu Leu Ser Val Arg
        130                 135                 140

Ala Lys Pro Ser Ala Pro Val Val Ser Gly Pro Ala Val Arg Ala Thr
145                 150                 155                 160

Pro Glu His Thr Val Ser Phe Thr Cys Glu Ser His Gly Phe Ser Pro
                    165                 170                 175

Arg Asp Ile Thr Leu Lys Trp Phe Lys Asn Gly Asn Glu Leu Ser Asp
                180                 185                 190

Phe Gln Thr Asn Val Asp Pro Ala Gly Asp Ser Val Ser Tyr Ser Ile
            195                 200                 205

His Ser Thr Ala Arg Val Val Leu Thr Arg Gly Asp Val His Ser Gln
        210                 215                 220

Val Ile Cys Glu Met Ala His Ile Thr Leu Gln Gly Asp Pro Leu Arg
225                 230                 235                 240

Gly Thr Ala Asn Leu Ser Glu Ala Ile Arg Val Pro Pro Thr Leu Glu
                    245                 250                 255

Val Thr Gln Gln Pro Met Arg Ala Glu Asn Gln Ala Asn Val Thr Cys
                260                 265                 270

Gln Val Ser Asn Phe Tyr Pro Arg Gly Leu Gln Leu Thr Trp Leu Glu
            275                 280                 285

Asn Gly Asn Val Ser Arg Thr Glu Thr Ala Ser Thr Leu Ile Glu Asn
        290                 295                 300

Lys Asp Gly Thr Tyr Asn Trp Met Ser Trp Leu Leu Val Asn Thr Cys
305                 310                 315                 320

Ala His Arg Asp Asp Val Leu Thr Cys Gln Val Glu His Asp Gly
                    325                 330                 335

Gln Gln Ala Val Ser Lys Ser Tyr Ala Leu Glu Ile Ser Ala His Gln
                340                 345                 350

Lys Glu His Gly Ser Asp Ile Thr His Glu Pro Ala Leu Ala Pro Thr
            355                 360                 365

Ala Pro Leu Leu Val Ala Leu Leu Leu Gly Pro Lys Leu Leu Leu Val
        370                 375                 380

Val Gly Val Ser Ala Ile Tyr Ile Cys Trp Lys Gln Lys Ala
385                 390                 395

<210> SEQ ID NO 5
<211> LENGTH: 30
<212> TYPE: DNA
<213> ORGANISM: Artificial
<220> FEATURE:
<223> OTHER INFORMATION: primer
```

```
<400> SEQUENCE: 5
ccggatccaa cagggttctt aacaccaacc                                              30

<210> SEQ ID NO 6
<211> LENGTH: 30
<212> TYPE: DNA
<213> ORGANISM: Artificial
<220> FEATURE:
<223> OTHER INFORMATION: primer

<400> SEQUENCE: 6
ccgaattctg ctcattagca cttatttcca                                              30

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
ccggatccaa cagggttctt aacaccaacc                                              30

<210> SEQ ID NO 8
<211> LENGTH: 29
<212> TYPE: DNA
<213> ORGANISM: Artificial
<220> FEATURE:
<223> OTHER INFORMATION: primer

<400> SEQUENCE: 8
aggtctagaa gcaatacctg ccgtcttca                                               29
```

PHARMACEUTICAL COMPOSITION AND METHOD FOR ACTIVATING MACROPHAGE USING THE SAME

The present invention relates to a pharmaceutical composition comprising an antibody which recognizes an extracellular domain of signal regulatory protein β (SIRPβ) and a pharmaceutical acceptable carrier. The present invention also relates to a method for activating macrophages and a method for treating infectious disease or cancer using the pharmaceutical composition. The present invention further relates to a method for screening a macrophage-activating agent.

BACKGROUND OF THE INVENTION

Macrophages have functions of clearing wastes in a body and of defending against pathogens including microorganisms and viruses or tumor cells. It displays antigens for T cells and produces interleukin-1, and thereby functions as an effector of cell-mediated immunity. Thus, it is important to activate macrophages for treatment of infectious diseases or cancers.

Interferon is one of the macrophage-activating factors and has been used for clinical trials. In addition, it is known that some kinds of polysaccharides have an ability to activate immune response and some of them have been developed as an anti-virus agent or anti-cancer agent (Japanese Patent Laid-open publication No. 05-097695 or Japanese Patent No.06-099314). However, it has hardly been tried to activate macrophages using an antibody.

A gene for human signal regulatory protein β (SIRPβ) has been cloned and SIRPβ was predicted to be a transmembrane protein having an extracellular domain with three Ig-like domains and a short intracellular domain from its deduced amino acid sequence (Nature, 1997, vol. 386, p181-186). The gene for SIRPβ was cloned based on a homology with signal regulatory protein α (SIRPα; also called as SHPS-1), however, physiological role of SIRPβ has not been elucidated because SIRPβ does not have YXX (L/V/I) motief which is a tyrosine-phosphorylation site and to which SH2 domain of proteins such as SHP-1 binds, contrary to SIRPα.

An antibody which recognizes an extracellular domain of SIRPα has been used for inhibiting macrophage-mediated phagocytosis (WO 00/66159). On the other hand, an antibody which recognizes an extracellular domain of SIRPβ has been produced and used for a research purpose (Blood, 2001, Vol. 97, No. 9, p. 2741-2749). However, such an antibody has never been used for activating macrophages, since physiological role of SIRPβ has not been known.

SUMMARY OF THE INVENTION

An object of the present invention is to provide a pharmaceutical composition which can be used for activating macrophages. Another object of the present invention is to provide a method for screening a macrophage-activating agent.

The inventors of the present invention assiduously studied and, as a result, they found that an antibody which recognizes an extracellular domain of SIRPβ has an effect of activating macrophages. Furthermore, they found that such an antibody could be used as an active ingredient of pharmaceutical composition. Thus, they have accomplished the present invention.

That is, the present invention relates to the following.

(1) A pharmaceutical composition comprising an antibody which recognizes an extracellular domain of SIRPβ and a pharmaceutical acceptable carrier.

(2) The pharmaceutical composition according to (1), wherein said antibody is a monoclonal antibody.

(3) A method of activating macrophage which comprises administering the pharmaceutical composition according to (1) to a subject.

(4) A method of treating a subject of infectious disease or cancer, which comprises administering the pharmaceutical composition according to (1) to a subject.

(5) A method of producing a pharmaceutical composition which comprises obtaining an antibody which recognizes an extracellular domain of SIRPβ and formulating the antibody with a pharmaceutical acceptable carrier.

(6) A method of screening a macrophage-activating agent, which comprises obtaining a substance which binds an extra cellular domain of SIRPβ and providing the substance to macrophage cells and measuring a macrophage-activating ability of the substance.

Macrophages can be efficiently activated by the pharmaceutical composition of the present invention. Since activation of macrophages can induce cell-mediated immunity, the pharmaceutical composition of the present invention is suitable as an anti-virus agent, anti-bacterial agent, anti-cancer agent and the like.

DETAILED DESCRIPTION OF THE PREFERRED EMBODIMENTS

Hereafter, embodiments of the present invention will be explained in detail.

The pharmaceutical composition of the present invention comprises an antibody which specifically recognizes an extracellular domain of SIRPβ. SIRPβ is preferably mammalian SIRPβ, more preferably human or mouse SIRPβ, and especially preferably human SIRPβ.

Examples of human SIRPβ include a protein having an amino acid sequence of SEQ ID No. 4 and examples of mouse SIRPβ include a protein having an amino acid sequence of SEQ ID No. 2. An antibody contained in the pharmaceutical composition of the present invention may be an antibody which can recognize one or more of SIRPβs including those originated from human and mouse.

Examples of extracellular domain of human SIRPβ include a domain having an amino acid sequence of amino acid numbers 1 to 369 of the sequence of SEQ ID No. 4, and examples of extracellular domain of mouse SIRPβ include a domain having an amino acid sequence of amino acid numbers 1 to 362 of the sequence of SEQ ID No. 2. An antibody contained in the pharmaceutical composition of the present invention is an antibody which can recognize the above-mentioned extracellular domain, and of which epitope may exist at any site of the extracellular domain so long as the antibody has an ability to activate macrophages.

For example, an antibody which specifically recognizes an extracellular domain of SIRPβ can be produced as follows. That is, at first, an extracellular domain of SIRPβ is produced by using host cells such as *Escherichia coli* cells or mammalian cells. Specifically, a DNA encoding an extracellular domain of SIRPβ is amplified by PCR using primers designed based on a nucleotide sequence of a gene encoding SIRPβ. Examples of DNA encoding an extracellular domain of mouse SIRPβ include a DNA having a nucleotide sequence of nucleotide numbers 23 to 1108 of the sequence of SEQ ID No. 1, and examples of DNA encoding an extracellular domain of human SIRPβ include a DNA having a nucleotide sequence of nucleotide numbers 41 to 1147 of the sequence of SEQ ID No. 3. A plasmid which can be obtained by inserting one of those DNAs into a conventional plasmid suitable for protein expression is introduced into host cells, and thereby an extracellular domain of SIRPβ is expressed. According to a conventional procedure, an extracellular domain of SIRPβ is isolated and purified. Plasmids used to express a protein in *Escherichia coli* cells include pET vector (Novagen) and pGEX vector (Invitrogen), and those used to express a protein in mammalian cells include pcDNA vector (Invitrogen). An extracellular domain of SIRPβ may be expressed as a fusion protein which has a peptide tag for purification or the like.

An antibody contained in the pharmaceutical composition of the present invention may be a monoclonal antibody or polyclonal antibody, more preferably a monoclonal antibody. A monoclonal antibody can be produced as follows. A non-human mammal is immunized with an extracellular domain of SIRPβ as produced above and then hybridoma cells are produced by fusing lymph cells isolated from the immunized animal to mouse myeloma cells. An antibody to be contained in the pharmaceutical composition of the present invention is obtained by screening an antibody which specifically recognizes an extracellular domain of SIRPβ and has an ability to activate macrophages, from the antibodies produced from the hybridoma cells. A portion of the extracellular domain of SIRPβ may be used to immunization. Whether an antibody specifically recognizes an extracellular domain of SIRPβ can be determined by conventional methods including western blotting or ELISA. Whether an antibody has an ability to activate macrophages can be determined by comparing cell morphology or a phagocytotic activity against opsonized red blood cells between antibody-treated macrophages and non-treated macrophages.

Monoclonal antibodies used in the present invention may be any antibodies so long as they can specifically recognize an extracellular domain of SIRPβ and has an ability to activate macrophages, and examples of those include mAb80 and mAb84 shown in the EXAMPLES.

In the present invention, "monoclonal antibody" includes a monoclonal antibody, a fragment thereof, $F(ab')_2$ antibody, F(ab') antibody, a short chain antibody (scFv), diabodies and minibodies. An antibody obtained from mouse myeloma cells may preferably be processed into chimeric antibody or humanized antibody for the purpose of using a pharmaceutical composition of the present invention for human. Specifically, chimeric antibodies can be produced by replacing a constant region of an antibody with that of human using gene recombination technique, and humanized antibody can be obtained by replacing a region other than hypervariable regions of an antibody with that of human.

The pharmaceutical composition of the present invention can be obtained by formulating an antibody which recognizes an extracellular domain of SIRPβ with a pharmaceutical acceptable carrier. Examples of pharmaceutical acceptable carriers include diluents, stabilizers, storing agents, buffers and the like. The antibody is preferably multimerized and formulated into the pharmaceutical composition, in order to enhance the antibody concentration in a target tissue and activate macrophages efficiently. The antibody can be multimerized, for example, by cross-linking the antibody molecules using a secondary antibody such as an antibody against Fc region of the antibody. The antibody may also be multimerized by cross-linking the antibody molecules using biotin-avidin method in which the antibody is labeled with biotin and cross-linked through avidin.

A form of the pharmaceutical composition of the present invention is not particularly limited, but preferably a formulation for injection. A formulation for injection can be prepared by solubilizing an antibody into a diluent and adding a stabilizing agent, storing agent or buffer if required. The formulation may be administered via intravenous injection, subcutaneous injection, intracutaneous injection, intramuscular injection or intraperitoneal injection, and more preferably via intravenous injection.

The pharmaceutical composition of the present invention is administered in an amount enough to activate macrophages, which amount can be properly adjusted according to several factors including age, sex, bodyweight or symptom of a patient, or way of administration or content of an antibody in the composition. More specifically, the pharmaceutical composition is preferably administered in an amount so that an amount of the antibody falls between 1 μg and 100 mg, more preferably between 50 μg and 50 mg per kg body weight of a patient in one dosage. The pharmaceutical composition of the present invention may be administered once or plural times per day.

The pharmaceutical composition of the present invention has an effect of activating macrophages. Therefore, it can be used as an agent for treating or preventing diseases which can be treated or prevented by macrophage-mediated removal of foreign substances including bacteria, viruses and cancer cells etc. Examples of these diseases include infectious diseases and cancer, and more specifically include chronic myeloid leukemia, hair cell leukemia, hepatitis type B, hepatitis type C, renal cell cancer and autoimmune hepatitis.

The present invention also relates to a method of screening a macrophage-activating agent, which comprises obtaining a substance which binds an extracellular domain of SIRPβ and providing the substance to macrophage cells and measuring a macrophage-activating ability of the substance. The substance which binds an extracellular domain of SIRPβ may be low molecular weight compounds, saccharides, peptides, proteins (including antibodies) and so on. The substance which binds an extracellular domain of SIRPβ may be obtained by, for example, immunoprecipitation using an extracellular domain of SIRPβ or two-hybrid method using a DNA encoding the domain.

Figure 4:
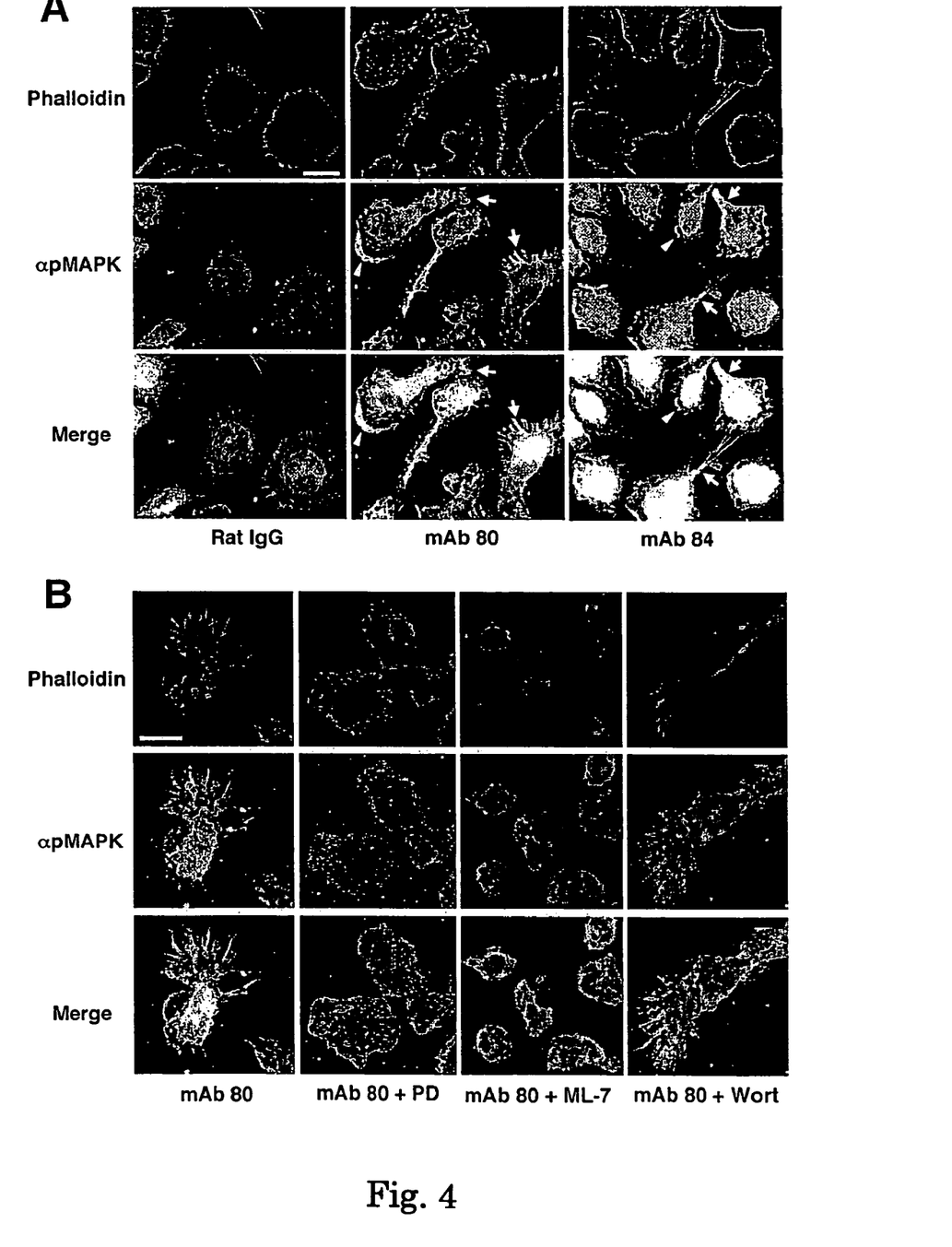
FIG. 4 shows the results of immunofluorescence staining. (A) Morphology and MAPK activation of PEMs treated with a control rat IgG or anti-SIRPβ extracellular domain antibodies (mAb80 and mAb84); (B) Morphology and MAPK activation of PEMs treated with an anti-SIRPβ extracellular domain antibody (mAb80) in the presence or absence of the indicated inhibitors. Merged images are also shown.
Figure 7:
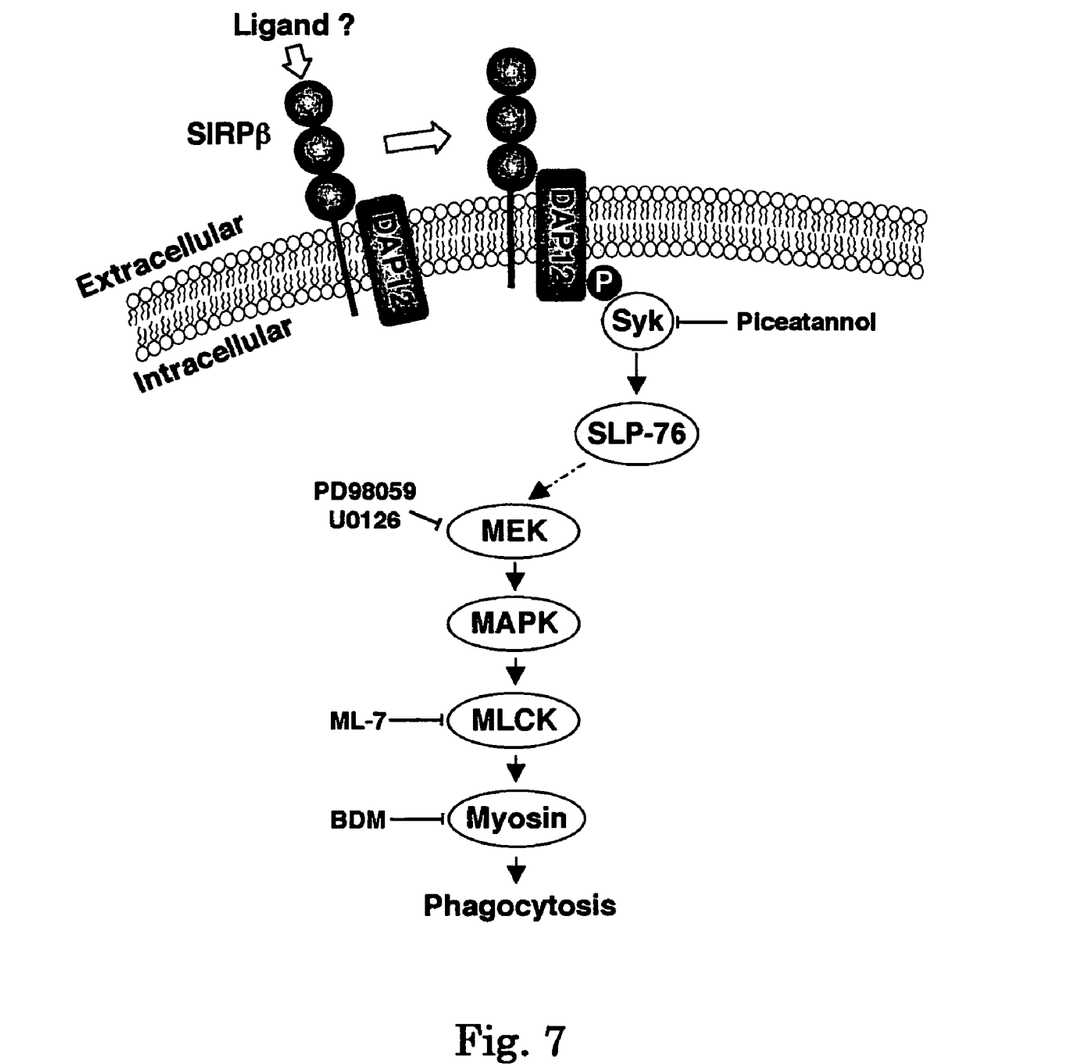
FIG. 7 shows a predicted mechanism for macrophage activation by an anti-SIRPβ extracellular domain antibody.

A macrophage-activating agent can be obtained by adding the substance as obtained above into macrophage cells, measuring an ability of the substance to activate macrophages and selecting a substance which can activate macrophages. Peritoneal macrophages prepared according to conventional methods or RAW264.7 cells (ATCC TIB-71) may be used as macrophage cells. A macrophage-activating ability can be determined by observing cell morphology or phagocytotic activity of the macrophages treated with the substance. Activated macrophages shows an elongated morphology having filopodia or lamellipodia as shown in FIG. 4, and thus, activation of macrophages can be determined by calculating the number of cells which shows this kind of morphology. In addition, activation of macrophages can be determined by adding red blood cells opsonized as described in the EXAMPLES to macrophages and calculating the number of macrophages containing phagocytosed red blood cells. Furthermore, Syk, SLP-76 and MAP kinase etc. are activated (phosphorylated) in the macrophage-activating pathway mediated by SIRPβ as shown in FIG. 7, and thus activation of macrophages may also be calculated by determining degrees of phosphorylation of these factors with western blotting.

EXAMPLES

The present invention will be explained more specifically with reference to the following examples. However, the scope of the present invention is not limited to these examples.

1. Cloning of a Mouse SIRPβ cDNA

A cDNA for C57BL/6 mouse SIRPβ was amplified by PCR from a λZapII spleen cDNA library (Stratagene) with the primers having a nucleotide sequence of SEQ ID NO: 5 and 6, respectively. The resulting PCR product was subcloned into pGEM-T (Invitrogen). The nucleotide sequences of the amplified cDNAs were verified by sequencing with an ABI PRISM310 Genetic Analyzer (Applied Biosystems). As a result, a nucleotide sequence of mouse SIRPβ cDNA was found to be SEQ ID NO: 1.

2. Preparation of SIRPβ-Fc Fusion Protein

A DNA fragment encoding the Fc portion was excised from the pEFneoFc76 vector (*EMBO J.*, 2003, vol. 22, p2634-2644) with EcoRI and NotI and was subcloned into pTracer-CMV (Invitrogen) to generate the vector pTracer-Fc.

A DNA fragment encoding the extracellular region of mouse SIRPβ (amino acids 1 to 362 of SEQ ID NO: 2) was amplified from the full-length C57BL/6 mouse SIRPβ cDNA as amplified above, by PCR using the primers having a nucleotide sequence of SEQ ID NO: 7 and 8, respectively. The obtained PCR product was digested with BamHI and XbaI, and the resulting DNA fragment was subcloned into pTracer-Fc to generate the vector pTracer-CMV-SIRPβ-Fc for expression of the fusion protein containing a mouse SIRPβ extracellular domain and Fc.

CHO-Ras cells (a cell stably expresses an activated H-Ras) were transfected with pTracer-CMV-SIRPβ-Fc and subjected to selection with Zeocin as described in *EMBO J.*, 2003, vol. 22, p2634-2644. Several cell lines producing SIRPβ-Fc were identified by immunoblot analysis of culture supernatants with HRP-conjugated goat pAbs specific for the Fc fragment of human IgG (Jackson Immuno Research). The SIRPβ-Fc fusion proteins were purified from the culture supernatants by column chromatography on protein A-Sepharose 4FF (Amersham Pharmacia Biotech).

3. Preparation of Anti-SIRPβ Extracellular Domain Antibodies

SIRPβ-Fc fusion protein was injected into the hind foot pads of two Wistar rats three times at 1-week intervals, after which lymphocytes were isolated from the draining lymph nodes and fused with P3U1 myeloma cells as described in *J. Biol. Chem.*, 1996, 271, 27652-27658. Hybridoma clones producing monoclonal antibodies that reacted with SIRPβ-Fc but not with SHPS-1-Fc were identified by ELISA. SHPS-1-Fc is a fusion protein comprising Fc and SHPS-1 (Blood, 2001, vol. 97, No.9, p2741-2749). Among seven positive clones, clones 80 and 84 were selected for experiments. The monoclonal antibodies were purified from serum-free culture supernatants of clones 80 and 84 by column chromatography on protein G-Sepharose 4FF (Amersham Pharmacia Biotech). These antibodies were named as mAb80 and mAb84, respectively. The isotype of both mAbs 80 and 84 was determined as IgG2a, κ with the use of a Rat MonoAB ID/SP kit (Zymed).

4. Activation of mMacrophages using Anti-SIRPβ Antibodies

Thioglycolate-elicited mouse primary PEMs were isolated and cultured as described in *J. Biol. Chem.*, 2002, 277, 39833-39839. In brief, the peritoneum was flushed with ice-cold PBS containing 0.2% BSA 3 days after i.p. (intraperitoneal) injection of C57BL/6 mice with 3 ml of 3% thioglycolate broth (Nissui, Tokyo, Japan). The exudate cells were isolated by centrifugation at 400×g for 5 min at 4° C., washed with ice-cold RPMI-1640 (SIGMA), and resuspended in RPMI-1640 supplemented with 10% FBS. After incubation for 24 h at 37° C., nonadherent cells, which include neutrophils, B cells, and T cells, were washed away. The obtained thioglycolate-elicited mouse PEMs were plated in 24-well culture plates and cultured for 3 to 4 days. Immediately before phagocytosis assays, the plates were placed on ice and mAb80 or mAb84 (or isotype-matched control rat IgG) were then added to the cells at a concentration of 20 μg/ml. After incubation for 15 min on ice, the cells were washed twice with ice-cold PBS and then serum-free RPMI-1640 containing glutaraldehyde-stabilized IgG-opsonized sheep RBCs (Ig-sRBCs) ($5×10^7$ per well) (Inter-Cell Technologies) was added in the presence (FIG. 1A, $2^{nd}$ Abs(+) and FIG. 1C, D) or absence (FIG. 1A, $2^{nd}$ Abs(−))of secondary antibody. For secondary antibodies, goat-polyclonal antibody for rat IgG (20 μg/ml; Jackson Immuno Research) was used. In FIGS. 1C and 1D, phagocytosis assay with non-opsonized sheep RBCs or C3bi-opsonized sheep RBCs was also performed.

In FIG. 1B, the mouse macrophage cell line RAW264.7 was used. RAW264.7 was cultured in RPMI-1640 supplemented with 10% FBS. Culture was performed under the humidified condition of 37° C., 5% $CO_2$. mAb80, mAb84 or control IgG was added at the concentration of 20 μg/m by the same procedure as for PEMs. Then, serum-free RPMI-1640 containing glutaraldehyde-stabilized IgG-opsonized sheep RBCs was added in the presence (FIG. 1B, $2^{nd}$ Abs (+)) or absence (FIG. 1B, $2^{nd}$ Abs (−))of secondary antibody.

IgG- or C3i-opsonized RBCs were prepared according to the procedure described in *J. Exp. Med.*, 2001, 193, 855-862.

Macrophages treated with non-opsonized, IgG-opsonized or C3i-opsonized RBCs were tested according to the following procedures. After incubation for 15 min on ice, culture plates were transferred to a water bath at 37° C. to initiate phagocytosis. Phagocytosis was terminated after the indicated time by again placing the plates on ice, and the cells were washed with ice-cold PBS three times. The PEMs were then fixed with 4% paraformaldehyde in PBS, after which phagocytosed RBCs were detected with a phase-contrast microscope and random fields were photographed. For phagocytosis assays with mouse RBCs., the PEMs were incubated for 5 min at room temperature with hemolysis buffer [154 mM $NH_4Cl$ (pH 7.3), 10 mM $KHCO_3$, 0.1 mM EDTA] before fixation in order to remove attached RBCs. To determine the phagocytosis index, we identified >100 cells in randomly chosen fields of view, and the percentage of cells that had engulfed RBCs was determined.

Figure 1:
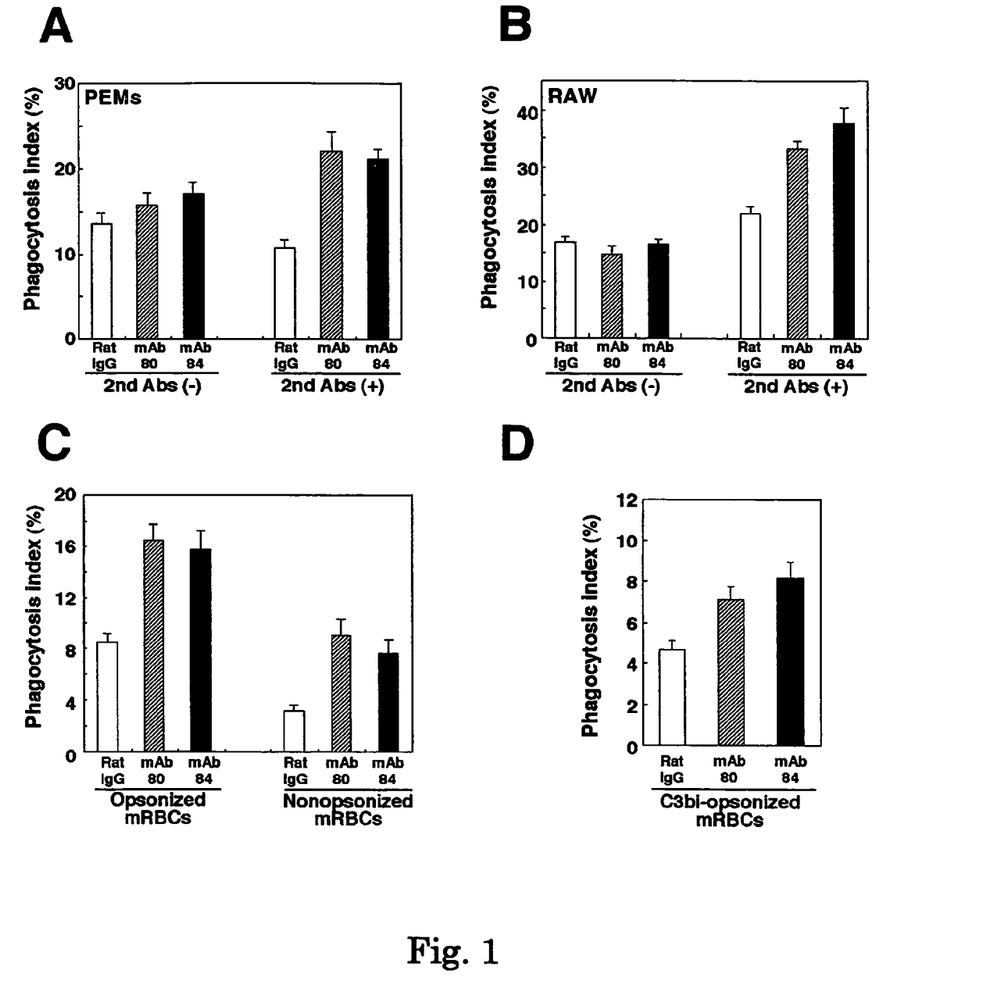
FIG. 1 shows the effect of anti-SIRPβ extracellular domain antibodies on phagocytosis of macrophages. A and B show the effects on phagocytosis of peritoneal macrophages (PEMs) or RAW264.7 cells, respectively. C shows the effects on phagocytosis of PEMs for IgG-opsonized RBCs (red blood cells) or nonopsonized RBCs. D shows the effect on phagocytosis of PEMs for complement C3bi-opsonized RBCs.

The results are shown in FIG. 1. As shown in FIG. 1A, macrophage-mediated phagocytosis of PEMs treated with an anti-SIRPβ antibody (mAb80 or mAb84) and cross-linked with a second antibody increased about two-fold as compared to PEMs treated with a control rat IgG and cross-linked with a second antibody. Few effects were observed without an addition of a second antibody, which suggested that enhancement of antibody concentrations, for example, by cross-linking the antibodies with a second antibody, would be required for macrophage activation by an anti-SIRPβ antibody. FIG. 1B shows that mAb80 and mAb84 can also activate a cultured macrophage cell line. As shown in FIG. 1C, PEMs activated by mAb80 and mAb84 can phagocytose opsonized RBCs more efficiently although they can phagocytose non-opsonized RBCs as well. FIG. 1D shows that PEMs activated by mAb80 and mAb84 can also phagocytose complement C3bi-opsonized RBCs.

5. The Effect on MAPK and MEK

The following procedure was performed to investigate the mechanism by which an anti-SIRPβ antibody activates macrophages.

Figure 2:
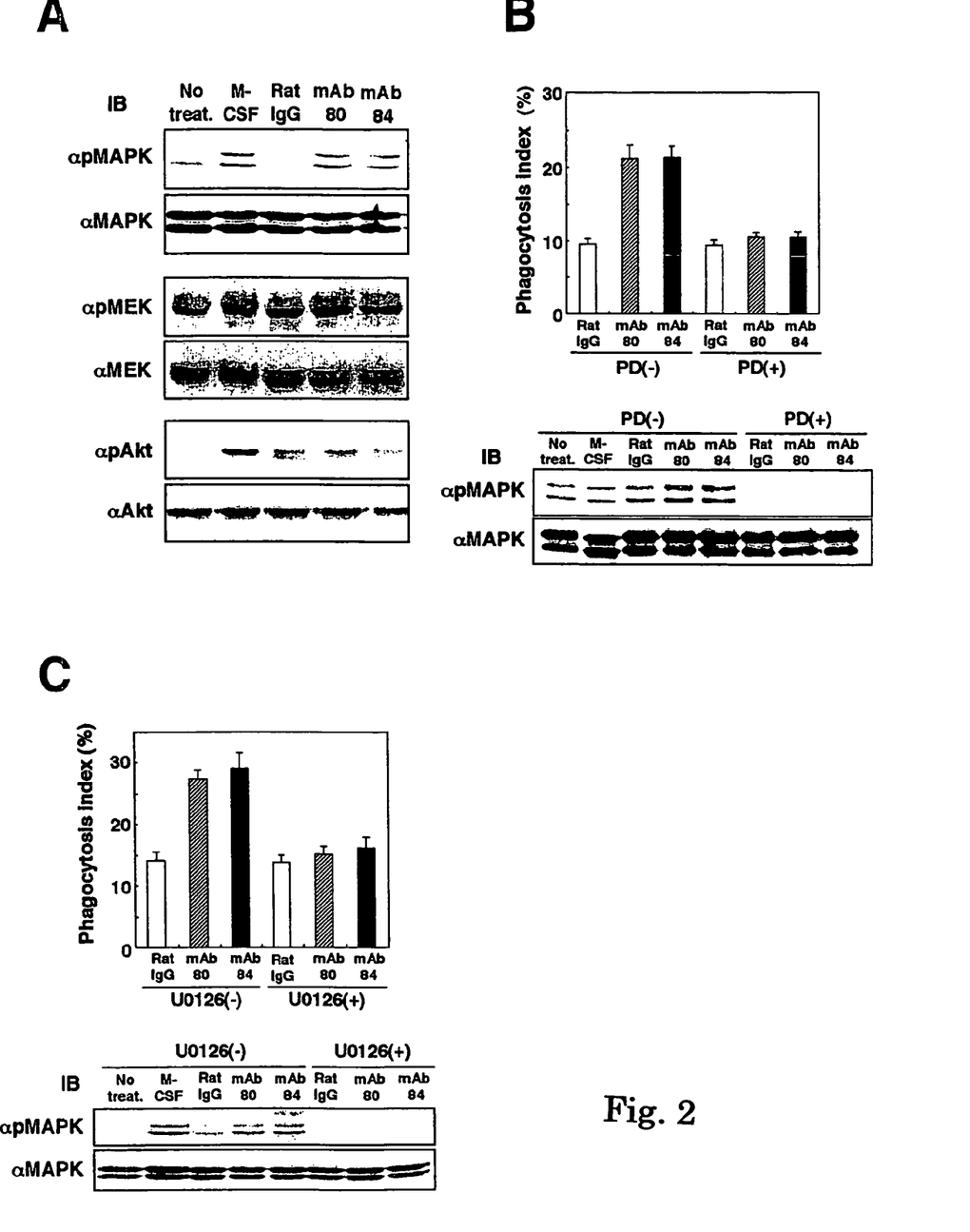
FIG. 2 shows the roles of MAPK and MEK in the macrophage-activation by an anti-SIRP β extracellular domain antibody. A shows the effect of an anti-SIR β extracellular domain antibody on MAPK or MEK. B shows the effect of MEK inhibitor, PD98059. C shows the effect of MEK inhibitor, U 0126.

PEMs were treated with anti-SIRPβ antibody or control IgG, and a secondary antibody, and incubated at 37° C. for 10 min. As a positive control, PEMs were incubated at 37° C. for 10 min in the presence of M-CSF (macrophage colony stimulating factor) (10 ng/ml). As a negative control, non-treated PEMs were used. Then, cells were lysed and subjected to immunoblot analysis using an anti-MAPK antibody (αMAPK), anti-activated (phosphorylated) MAPK antibody (αpMAPK), anti-MEK antibody (αMEK) or anti-activated MEK antibody (αpMEK) (FIG. 2A). It was found that phosphorylation of MAPK and MEK was elevated by mAb80 and mAb84, which suggested that addition of an anti-SIRPβ antibody leads to activation of MAPK and MEK.

Then, the MEK inhibitors, PD98059 and U0126 were used to examine the role of MAPK-MEK pathway in the macrophage activation by an anti-SIRPβ antibody. PEMs were incubated in the presence or absence of 50 μM PD98059 or 2 μM U0126 at 37° C. for 30 min, and then treated with an anti-SIRPβ antibody or control IgG, and a secondary antibody. After incubation with IgG-opsonized RBCs at 37° C. for 5 min, cells were fixed and phagocytosis index was calculated (FIG. 2B, C; upper figures). On the other hand, PEMs were treated with an anti-SIRPβ antibody or control IgG, and a secondary antibody in the presence or absence of the inhibitors, followed by an analysis using an anti-MAPK antibody (αMAPK) and an anti-activated (phosphorylated) MAPK antibody (αpMAPK) (FIG. 2B, C; bottom figures). As a result, activation of MAPK did not occur by addition of mAb80 and mAb84 and macrophages-mediated phagocytosis was not activated by the anti-SIRPβ antibodies in the presence of MEK inhibitors. These results suggested that MEK-MAPK pathway is involved in the activation of macrophage-mediated phagocytosis by an anti-SIRPβ antibody.

6. The Effect on Myosin Light Chain Kinase (MLCK)

Activation of MLCK by MAPK is implicated in the positive regulation of cell adhesion and cell migration mediated by cytoskeletal reorganization (*J. Cell Biol.*, 1997, 137, 481-492). Then, it was analyzed whether activation of MLCK by MAPK is involved in the activation of macrophage-mediated phagocytosis by an anti-SIRPβ antibody.

Figure 3:
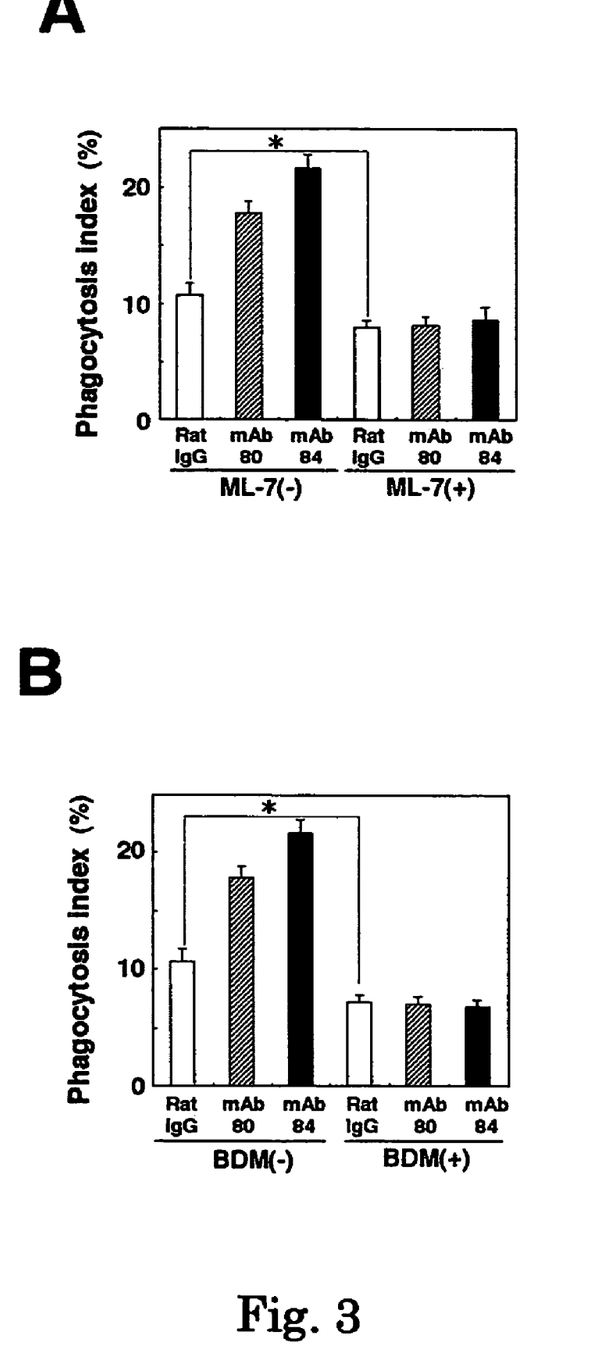
FIG. 3 shows the roles of MLCK and myosin in the macrophage-activation by an anti-SIRPβ extracellular domain antibody. A shows the effect of MLCK inhibitor, ML-7. B shows the effect of an inhibitor of ATPase activity of myosin, BDM (2,3-butanedione 2-monoxime).

PEMs were incubated in the presence or absence of MLCK inhibitor, ML-7 (10 μM; *J. Biol. Chem.*, 1987, 262, 7796-7801) at 37° C. for 30 min, and then treated with an anti-SIRPβ antibody or control IgG, and a secondary antibody. After incubation with IgG-opsonized RBCs at 37° C. for 5 min, cells were fixed and phagocytosis index was calculated (FIG. 3A). Similar experiment was performed using the inhibitor (BDM, 50 mM) of ATPase activity of myosin which is activated by MLCK (FIG. 3B). As a result, addition of these inhibitors attenuated the activation of macrophages-mediated phagocytosis, which suggested that MLCK-Myosin pathway is involved in the activation of macrophage-mediated phagocytosis by an anti-SIRPβ antibody.

7. Immunocytofluorescence

PEMs treated with rat IgG, mAb80 or mAb84 were fixed for 20 to 30 min at room temperature in PBS containing 4% paraformaldehyde and 0.1% glutaraldehyde, and were then permeabilized for 60 min at room temperature in PBS containing 0.1% Triton X-100 and 5% goat serum (blocking solution). After incubation for 1 h at room temperature or overnight at 4° C. with primary antibody (anti-activated MAPK antibody) diluted in blocking solution, the cells were washed with PBS and incubated for 1 h at room temperature with Alexa488-conjugated secondary antibodies (Molecular Probes) diluted in blocking solution. For visualization of F-actin, cells were incubated with rhodamine-conjugated phalloidin (Molecular Probes) together with the secondary antibodies. The cells were finally washed with PBS and mounted. Fluorescence images were acquired with a laser-scanning confocal microscope (LSM5 PASCAL, Zeiss) (FIG. 4). As a result, it was found that the addition of mAb80 or mAb84 induced redistribution of MAPK into nucleus as well as the elongated morphology with filopodia and lamellipodia of macrophages. Such morphological change was markedly inhibited by treatment of PEMs with either MEK inhibitor (PD98059) or MLCK inhibitor (ML-7) but not by treatment with PI3 kinase inhibitor, wortmannin.

8. The Effect on DAP12 and Syk

SIRPβ forms a complex with DAP12 and engagement of SIRPβ induces tyrosine phosphorylation of DAP12 and its subsequent association with the tyrosine kinase Syk in cells overexpressing SIRPβ and DAP12 (*J. Immunol.*, 2000, 164, 9-12). Then, it was analyzed whether DAP12 and Syk are involved in the activation of macrophage-mediated phagocytosis by anti-SIRPP antibody.

Figure 5:
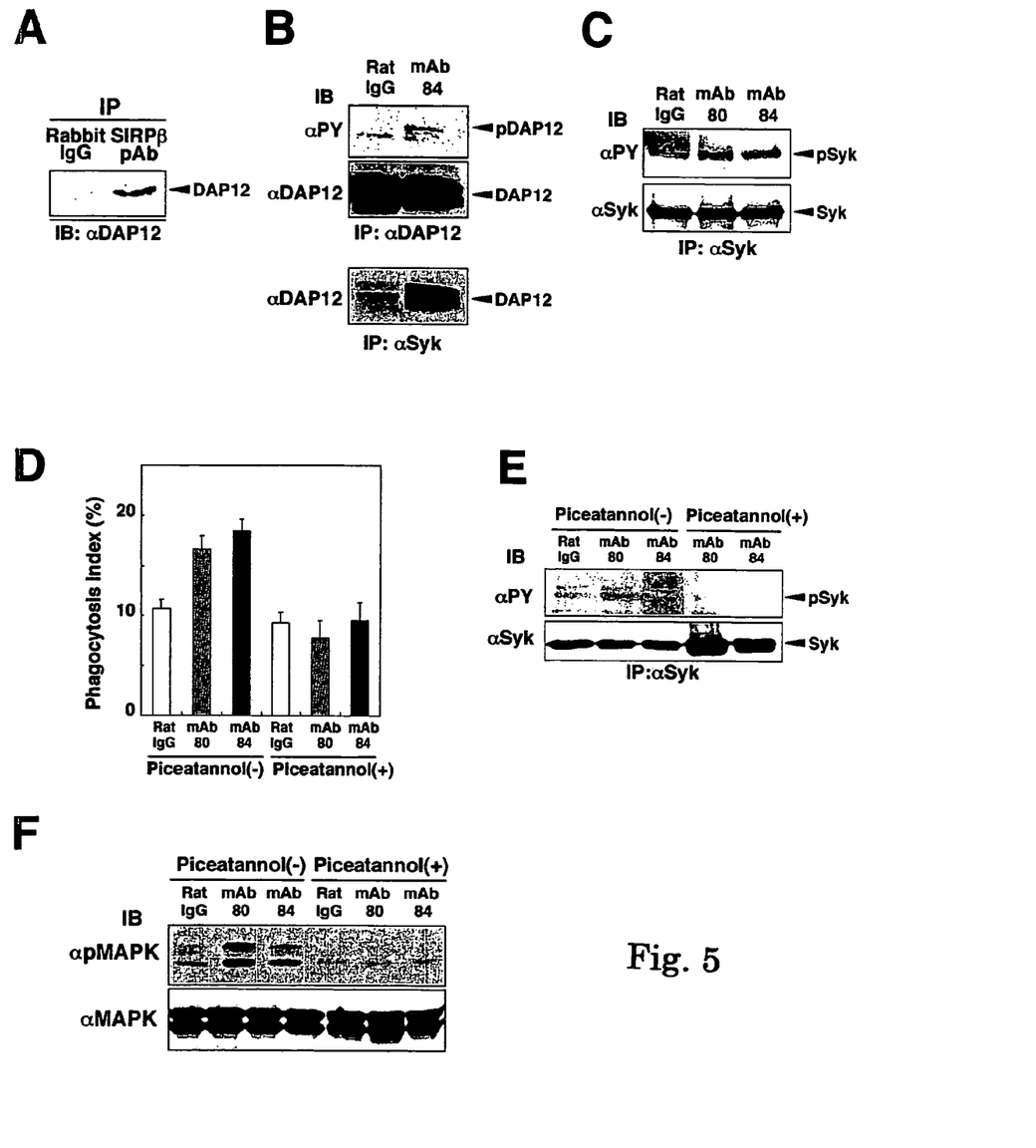
FIG. 5 shows the roles of DAP12 and Syk in the macrophage-activation by anti-SIRPβ extracellular domain antibody. (A) Immunoblot using an anti-DAP12 antibody; (B) Immunoblot using an anti-DAP12 antibody or an anti-phosphorylated tyrosine antibody; (C) Immunoblot using an anti-Syk antibody or an anti-phosphorylated tyrosine antibody; (D) Degree of macrophage-mediated phagocytosis in the presence or absence of piceatannol; (E) Immunoblot using an anti-Syk antibody or an anti-phosphorylated tyrosine antibody in the presence or absence of piceatannol; (F) Immunoblot using anti-MAPK antibody or anti-phosphorylated MAPK antibody in the presence or absence of piceatannol.

Immunoprecipitation was performed for PEM lysate treated with mAb84 or rat IgG, and a secondary antibody, by using an anti-SIRPβ polyclonal antibody, followed by immunoblot analysis using an anti-DAP12 antibody (FIG. 5A). As a result, it was found that SIRPβ and DAP12 interact with each other.

Immunoprecipitation was also performed for PEM lysate treated with mAb84 or rat IgG, and a secondary antibody, by using an anti-DAP12 polyclonal antibody, followed by immunoblot analysis using an anti-phosphorylated tyrosine antibody (FIG. 5B upper). In a similar manner, immunoprecipitation was performed for PEM lysate treated with mAb84 or rat IgG, and a secondary antibody, by using an anti-Syk polyclonal antibody, followed by immunoblot analysis using an anti-DAP12 antibody (FIG. 5B bottom). These results show that addition of mAb84 accelerated the phosphorylation of DAP12 and an interaction of DAP12 and Syk.

Furthermore, immunobolt analysis was performed for the immunoprecipitate obtained by an anti-Syk polyclonal antibody, using an anti-phosphorylated tyrosine antibody (FIG. 5C). As a result, it was shown that the addition of mAb80 and nMAb84 accelerated the phosphorylation of Syk.

Then, an effect of Syk inhibitor, piceatannol on anti-SIRPβ antibody-mediated macrophage activation was investigated. PEMs were incubated in the presence or absence of piceatannol at 37° C. for 30 min, and then treated with an anti-SIRPβ antibody or control IgG, and a secondary antibody. After incubation with IgG-opsonized RBCs at 37° C. for 5 min, cells were fixed and phagocytosis index was calculated (FIG. 5D). As a result, mAb80 or mAb84-mediated activation of phagocytosis was not observed in the presence of piceatannol.

Furthermore, immunoprecipitation was performed for PEMs treated with an anti-SIRPβ antibody or rat IgG, and a secondary antibody in the presence or absence of piceatannol, by using anti-Syk polyclonal antibody, followed by immunoblot analysis using an anti-phosphorylated tyrosine antibody (FIG. 5E). In addition, PEMs treated with an anti-SIRPβ antibody or control IgG, and a secondary antibody in the presence or absence of piceatannol were analyzed by immunoblotting using an anti-MAPK antibody (αMAPK) and anti-activated (phosphorylated) MAPK antibody (αpMAPK) (FIG. 5F). As a result, activation of Syk and MAPK by mAb80 and mAb84 was observed in the absence of piceatannol but not in the presence of piceatannol, which suggested that a sequential pathway including SIRPβ, DAP12, Syk and MAPK is involved in the activation of macrophage-mediated phagocytosis by an anti-SIRPβ antibody.

9. SLP-76 Activation by Syk

Figure 6:
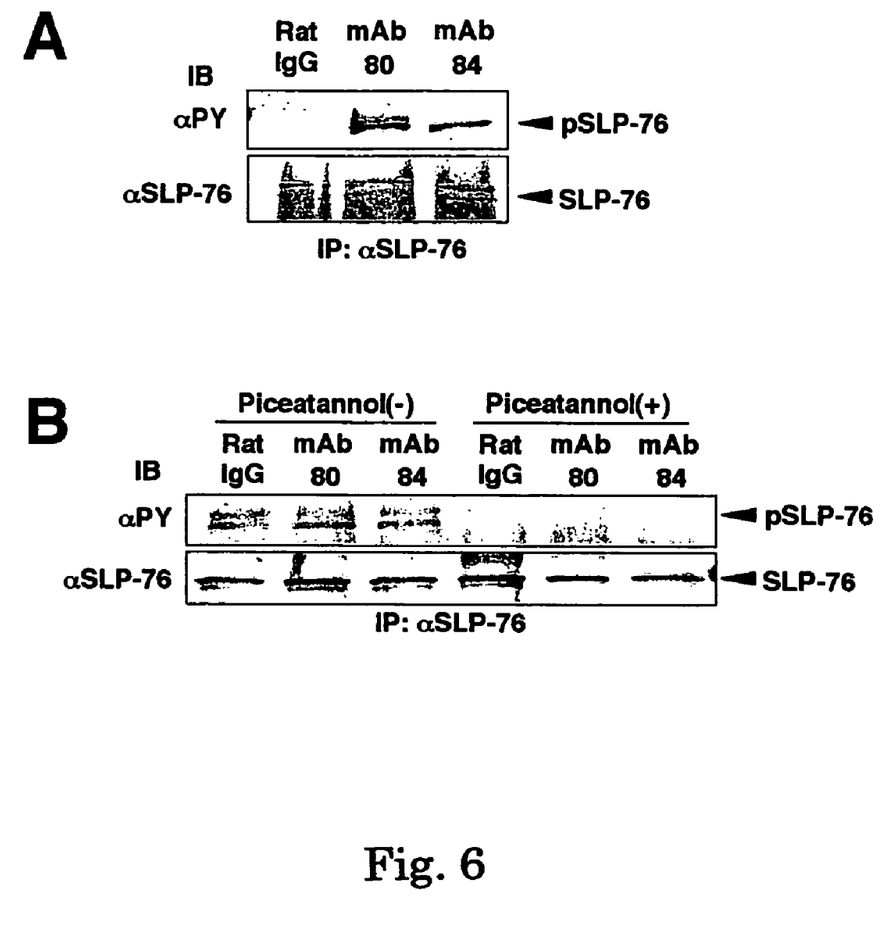
FIG. 6 shows the effect of an anti-SIRPβ extracellular domain antibody on SLP-76.(A) Immunoblot using an anti-SLP-76 antibody or an anti-phosphorylated tyrosine antibody; (B) Immunoblot using an anti-SLP-76 antibody or an anti-phosphorylated tyrosine antibody in the presence or absence of piceatannol.

Syk and the related tyrosine kinase ZAP-70 phosphorylate the adapter protein SLP-76 (*Immunity.,* 1998, 9, 607-616). Then, the following experiment was performed in order to examine whether SLP-76, an adaptor protein, can be activated by Syk activated by an anti-SIRPβ antibody. Immunoprecipitation was performed for PEMs treated with an anti-SIRPβ antibody or rat IgG, and a secondary antibody in the presence or absence of piceatannol, by using an anti-SLP-76 antibody, followed by immunoblot analysis using an anti-phosphorylated tyrosine antibody (FIG. 6A, B). As a result, activation of SLP-76 by mAb80 and mAb84 was observed in the absence of piceatannol but not in the presence of piceatannol.

According to the above results, the following mechanism was suggested in the SIRPβ-mediated activation of macrophage phagocytosis. That is, upon stimulation of an extracellular domain of SIRPβ with a ligand, DAP12, which is associated with SIRPβ, is phosphorylated, and then Syk binds to the phosphorylated site of DAP12. Subsequently, Syk phosphorylates SLP-76 and downstream MEK is activated, leading to activation of MAPK. The activated MAPK activates MLCK, which phosphorylates Myosin, thereby cytoskeleton structure changes and macrophages are activated.

The reagents used in the above experiments were as follows: A monoclonal antibody to DAP12 was produced according to the method described in *J. Immunol.,* 2000, 165, 3790-3796. Polyclonal antibodies to MAPK and activated MAPK were purchased from Promega. Polyclonal antibodies to MEK and activated MEK, and anti-phosphorylated tyrosine monoclonal antibody (PY-100) were purchased from Cell Signaling Technologies. Polyclonal antibodies to Syk (N-19) and SLP-76 (H-300) were purchased from Santa Cruz. Control rat IgG (IgG2a, κ) were purchased from Pharmingen. PD98059 and ML-7 were from Calbiochem; U0126 were from Promega; wortmanin, BDM and piceatannol were from Sigma. M-CSF was purchased from R&D Systems.

While the invention has been described in detail with reference to preferred embodiments thereof, it will be apparent to one skilled in the art that various changes can be made, and equivalents employed, without departing from the scope of the invention. Each of the aforementioned documents, including the foreign priority document, JP 2004-133599, is incorporated by reference herein in its entirety.

We claim:

1. An in vitro method of activating macrophage which comprises administering an antibody which recognizes an extracellular domain of SIRPβ to isolated macrophage.

* * * * *